United States Patent [19]

Albanese et al.

[11] Patent Number: 5,895,644
[45] Date of Patent: Apr. 20, 1999

[54] CLEAR ANTIPERSPIRANT STICK WITH DIBENZYLIDENE SORBITOL AND GUAR AND PROCESS OF MAKING SAME

[75] Inventors: Joseph Albanese, Belle Mead; Tom Schamper, Cranbury, both of N.J.

[73] Assignee: Colgate-Palmolive Company, New York, N.Y.

[21] Appl. No.: 08/974,945

[22] Filed: Nov. 20, 1997

[51] Int. Cl.$^6$ .................... A61K 7/00; A61K 7/32
[52] U.S. Cl. ............... 424/401; 424/65; 424/DIG. 5; 514/944; 514/947; 514/948
[58] Field of Search ............ 424/401, 65, DIG. 5; 514/944, 947, 948

[56] References Cited

U.S. PATENT DOCUMENTS

| | | | |
|---|---|---|---|
| 4,374,825 | 2/1983 | Bolich, Jr. et al. | 424/70.1 |
| 4,556,510 | 12/1985 | Holsopple | 252/547 |
| 4,678,606 | 7/1987 | Akhter et al. | 252/542 |
| 4,883,536 | 11/1989 | Burdick | 106/194 |
| 5,059,414 | 10/1991 | Dallal et al. | 424/70.1 |
| 5,380,528 | 1/1995 | Alban et al. | 424/401 |
| 5,420,118 | 5/1995 | Alban et al. | 514/63 |
| 5,534,265 | 7/1996 | Fowler et al. | 424/489 |

*Primary Examiner*—Shelley A. Dodson
*Attorney, Agent, or Firm*—Rosemary M. Miano

[57] ABSTRACT

The present invention contemplates a translucent, preferably clear, anhydrous gel composition (for example a solid stick, soft solid, cream as well as any form commonly referred to as a gel), especially an antiperspirant stick composition, comprising: (a) dibenzylidene sorbitol; (b) a selected derivatized guar, especially an hydroxy $C_3$–$C_4$ alkyl guar having a level of hydroxyalkylation of 0.4–1.5 molar substitution ("MS"); and (c) a solvent selected so that is will not react with the DBS itself or, if an acid catalyst is present, will not react in the presence of DBS with an acid catalyst such as an antiperspirant active salt.

29 Claims, No Drawings

1

CLEAR ANTIPERSPIRANT STICK WITH DIBENZYLIDENE SORBITOL AND GUAR AND PROCESS OF MAKING SAME

FIELD OF THE INVENTION

The present invention is directed to a clear, cosmetic gel stick composition suitable for use in a variety of cosmetic products. Examples of such products are underarm products useful for reducing malodor such as antiperspirants and/or deodorants which reduce/eliminate odor and/or wetness. The compositions are gelled with a dibenzylidene sorbitol and a selected guar as a structural integrity enhancer and have superior aesthetics. The invention also includes methods of making such stick compositions.

BACKGROUND OF THE INVENTION

Dibenzylidene sorbitol (also called dibenzaldehyde monosorbitol acetal, or dibenzyl monosorbitol acetal or dibenzylidene monosorbitol acetal) and derivatives thereof such as those which are substituted on one or both of the aromatic rings with a fluorine or methoxy group and those which have the sorbitol portion replaced with other reduced sugars such as xylitol or ribitol as described in U.S. Pat. No. 5,609,855 assigned to Procter & Gamble (collectively referred to as dibenzylidene sorbitol or "DBS") may be used in various food and cosmetic applications. For cosmetic uses the more interesting ones are those focused on obtaining a translucent or clear products. While dibenzylidene sorbitol is stable in alkaline or neutral media, such compounds are not stable in acidic media. In an acidic environment, such as in the presence of acidic antiperspirant materials, and when in the presence of even small amounts of water, the dibenzylidene sorbitol deteriorates and breaks down. Also, the use of DBS sometimes causes problems in the aesthetics of cosmetic products or problems with structural properties. Accordingly, there is a need to find a way to form products containing DBS which are stable and which have acceptable aesthetics.

There have been various attempts to work with DBS. Some of these efforts have focused on the stability of DBS. United Kingdom Patent GB 2 280 111, assigned to Union Camp Corporation, describes a gel stick composition comprising a dihydric alcohol as a primary solvent, a co-solvent such as low molecular weight polyethylene glycol, water and/or glycerine, a buffering agent and DBS as a gelling agent.

U.S. Pat. No. 4,720,381 to Schamper et al notes stability problems with this approach and itself describes the use of solvents having less reactive alcohol groups or alcohols with selected chain lengths in a DBS composition.

U.S. Pat. No. 4,816,261 to Luebbe et al describes stable deodorant gel stick compositions comprising DBS with a polar solvent and a coupling agent such as polypropylene glycol ethers of fatty alcohols.

U.S. Pat. No. 4,518,582 to Schamper, et al discloses an antiperspirant stick composition containing dibenzyl monosorbitol acetal in the presence of acidic antiperspirant-active salts, which composition is stable for extended periods of time at elevated temperatures. The composition contains at least a reactive solvent (such as water, methanol, ethanol, n-propanol, ethylene glycol, 1,2-propylene glycol, 1,3-propylene glycol, etc.), dibenzyl monosorbitol acetal, an antiperspirant-active compound, and a gel stabilizer, the gel stabilizer such as magnesium sulfate, zinc acetate and hexamethylenetetramine and mixtures thereof. This patent discloses that the stabilizer prevents or retards deterioration of the gelled sticks, especially when exposed to elevated temperatures.

Another patent disclosing stabilizers for solid gel antiperspirant sticks containing an acidic antiperspirant-active compound in the presence of dibenzyl monosorbitol acetal is U.S. Pat. No. 4,719,102 to Randhawa, et al. This patent discloses that the sticks include a solvent which is a small, polar organic compound such as cyclic esters, amides, amines, ketones, ureas, carbamates, sulfoxides and sulfones, and their open chain analogs; a cosolvent such as primary or low molecular weight alcohols and/or glycols; dibenzyl monosorbitol acetal; an antiperspirant-active compound; and a gel stabilizer such as N-(2-hydroxyethyl) fatty ($C_8$–$C_{20}$) acid amides, magnesium sulfate, zinc acetate, acetamide monoethanol amine and hexamethylenetetramine, and mixtures thereof.

U.S. Pat. No. 4,722,835 to Schamper, et al also discloses antiperspirant gel stick compositions gelled with dibenzyl monosorbitol acetal and containing an acidic antiperspirant compound, and also containing a stabilizer for the gel. This patent teaches that the compositions include a solvent which is a small, polar organic compound, as discussed previously in connection with U.S. Pat. No. 4,719,102; dibenzyl monosorbitol acetal; an antiperspirant-active compound; and a gel stabilizer such as (such as zinc oxide, calcium acetate, magnesium oxide, calcium carbonate, calcium hydroxide, magnesium carbonate, sodium carbonate, zinc carbonate and potassium carbonate). This patent discloses that these basic metallic salt gel stabilizers can stabilize the gel, even at high temperatures.

Other patent documents also disclose antiperspirant sticks gelled with a dibenzylidene sorbitol and include stabilizers for the gel.

EP Application No. 451,002 A2 discloses a stable, substantially anhydrous and substantially lower monohydric alcohol free, transparent, gelled, antiperspirant composition gelled by dibenzylidene monosorbitol acetal, containing acidic antiperspirants, and utilizing dihydric alcohols containing 3 to 6 carbon atoms as solvents, with the acetal being stabilized against hydrolysis and the formation of benzaldehyde by the presence of a stabilizing amount of a selected organic base, the organic base being a weakly basic, nitrogen-containing, organic compound.

EP Application No. 512,770 A1 discloses a stable, substantially anhydrous and substantially lower aliphatic monohydroxy alcohol free cosmetic composition gelled by dibenzylidene monosorbitol acetal, and containing acidic antiperspirant compounds and utilizing dihydroxy aliphatic alcohols containing 3–6 carbon atoms as solvents, wherein the dibenzylidene monosorbitol acetal gelling agent is stabilized against hydrolysis and the formation of benzaldehyde by the presence of a stabilizing amount of a selected inorganic base, the inorganic base including alkali and alkaline earth metal oxides, hydroxides, carbonates or bicarbonates, and trivalent metallic hydroxides.

PCT No. WO92/19221 discloses solid antiperspirant compositions in gel stick form, having an acid pH, and including (1) an antiperspirant active; (2) a gelling agent selected from the group consisting of substituted and unsubstituted dibenzylidene alditols; (3) a solvent for the gelling agent, preferably including a solvent material selected from the group consisting of monohydric and polyhydric alcohols, and mixtures thereof; and (4) a gelling agent stabilizer, the stabilizer being a basic metallic salt of an acid having a pKa of from about 3.8 to about 6.5 at 25 degrees C., the salt being at least partially soluble in the composition and being selected from the group consisting of $C_4$–$C_6$) dicarboxylate salts, $C_6$–$C_8$ monocarboxylate salts, and substituted or unsubstituted benzoate salts, and mixtures thereof, the gelling agent stabilizer not containing amino or amido functionalities. This patent document teaches that for clear or translucent sticks, the gelling agent stabilizer present in the composition should be fully soluble in the composition, in order to minimize refraction of light.

The foregoing patent documents also disclose methods for forming the disclosed antiperspirant stick compositions containing the antiperspirant materials and gelling agent. In particular, attention is directed to U.S. Pat. No. 4,719,102 and U.S. Pat. No. 4,722,835. Each of these patents discloses processes of forming the stick compositions, including dissolving the antiperspirant active in one phase and the dibenzyl monosorbitol acetal gellant in another phase. The two phases are then combined and poured into a mold or into the final package. The other components are added to either of the two phases depending on the compatibility of the component with the phases. More phases can be utilized, if desired, by forming a separate solution of some of the components, with the separate phases then being added to either of the two main phases; or all of the phases could be poured together at the end, as, for example, with a multistream filling head or an in-line mixer.

PCT No. WO92/19221 discloses a process of forming an antiperspirant gel stick, including preparing a solution containing the gelling agent, a solvent for the gelling agent, and the gelling agent stabilizer; mixing an antiperspirant active into such solution; and cooling the solution to form a gel.

There have also been efforts to develop DBS compositions to improve the aesthetics and/or mechanical properties while not sacrificing stability.

U.S. Pat. No. 4,346,097 to Roehl discloses a solid translucent gelled antiperspirant composition comprising DBS with an oleaginous compound (such as selected siloxanes, selected esters with an aliphatic character and branched chain hydrocarbons) to reduce stickiness.

PCT Publication Number 96/26709 to Vu et al describes a clear gel cosmetic stick which includes a liquid vehicle, an antiperspirant salt dissolved in the liquid vehicle, DBS and one or both of hydroxypropyl cellulose and a chelating agent. The hydroxypropyl cellulose maintains the hardness of the stick.

U.S. Pat. No. 4,863,721 to Beck et al describes the use of particulate cellulose ether polymers such as hydroxyethyl cellulose in antiperspirant compositions which are substantially free of polar solvents.

European Patent 0 260 030 B1 assigned to Unilever N. V. describes a transparent deodorant stick containing DBS and a thickening agent such as a chemically modified cellulose, polyacrylic acid, and/or polyacrylic acid copolymers and mixtures of the foregoing.

None of these references however, describes the use of guar such as a hydroxypropyl guar in connection with DBS and other components for a clear underarm product such as an antiperspirant stick. In particular it is noted that cellulose and guar are based on different carbohydrate building blocks that are arranged in a different way and, hence, give different properties in selected applications. Cellulose is water insoluble and gives plants the ability to maintain height. Cellulose is a linear polymer made of glucose units linked in a beta arrangement 1 to 4. Guar, on the other hand, is water soluble and is used to protect propagating plant seed. Guar is a branched polymer made from a linear backbone of mannose units linked in a beta arrangement 1 to 4 with random side chain attachments of galactose units linked to the mannose units in an alpha arrangement 1 to 6. Derivatives such as propylene glycol or butylene glycol ethers of either cellulose or guar would also reflect these structural differences.

Prior teachings of guar components in cosmetic applications include hair and or body care such as cleansing agents (see for example, U.S. Pat. No. 4,374,825 to Bolich et al; U.S. Pat. No. 4,556,510 to Holsopple; and U.S. Pat. No. 4,678,606 to Akhter et al.

While, as seen in the foregoing, there has been numerous efforts to find satisfactory cosmetic compositions suitable for use in forming underarm products such as deodorants and antiperspirants, for example, antiperspirant sticks, including clear antiperspirant gel sticks, containing acidic antiperspirant active ingredients and gelled with a dibenzylidene sorbitol, it is still desired to provide improved products, including, but not limited to, a clear stick composition containing an acidic antiperspirant active ingredient and gelled with dibenzylidene sorbitol and a selected guar which has increased stability over extended periods of times, and wherein deterioration of the gelling agent, and production of benzaldehyde due to such deterioration, are reduced. It is also still desired to provide an efficient manufacturing process for such cosmetic compositions.

It is a further object of the present invention to provide a clear antiperspirant and/or deodorant solid gel stick composition, which may contain an antiperspirant active salt and which is gelled by dibenzylidene sorbitol and a guar, the stick having structural integrity over extended periods of time (that is, to provide a rigid solid stick maintaining rigidity over extended periods of time).

It is a still further object of the present invention to provide a method of manufacturing clear antiperspirant solid gel stick compositions, utilizing dibenzylidene sorbitol and guar as a gelling system, wherein the processing for forming the stick is simplified.

SUMMARY OF THE INVENTION

The present invention contemplates a translucent, preferably clear, anhydrous gel composition (for example a solid stick, soft solid, cream as well as any form commonly referred to as a gel), especially an antiperspirant stick composition, comprising:

(a) dibenzylidene sorbitol;

(b) a selected derivatized guar, especially an hydroxy $C_3$–$C_4$ alkyl guar having a level of hydroxyalkylation of 0.4–1.5 molar substitution ("MS"); and (c) a solvent selected so that is will not react with the DBS itself or, if an acid catalyst is present, will not react in the presence of DBS with an acid catalyst such as an antiperspirant active salt.

Optionally one or more of the following ingredients including mixtures thereof and multiples of any single ingredient may also be included in compositions of the present invention:

1) an antiperspirant active;

2) an agent for reducing malodor;

3) a stabilizing agent;

4) an antibacterial agent;

5) an emollient;

6) a detackifier;

7) a sun screen;

8) a bug repelling agent;

9) an antisynerisis agent;

10) an anti-irritant;

11) fragrance; and
12) coloring.

DETAILED DESCRIPTION OF THE INVENTION

The first component of the composition is a dibenzylidene sorbitol, or a derivative thereof which has been explained above. The DBS functions as a gelling agent in the system and imparts desirable properties to the cosmetic gels formed. Examples of dibenzylidene sorbitol and derivatives thereof are described in PCT No. WO92/19221, the contents of which are incorporated herein by reference in their entirety. Examples of commercially available DBS products include MILLITHIX 925 (from Milliken Chemical, a division of Milliken & Company, Spartanburg, S.C.); DISORBENE (Roquette, Gurnee, Ill.).

The DBS is used in an amount of from 0.75–5.0%, particularly 0.75–3.0% and, more particularly, from 1.0–2.0% by weight based on the total weight of the composition.

The DBS is combined with an hydroxy $C_3$–$C_4$ lineal or branched alkyl guar having a level of hydroxyalkylation of 0.4–1.5 molar substitution ("MS"), preferably in the range of 0.6–1.5, more preferably 0.8–1.5 with 1.1–1.3 being especially preferred to obtain a clear product. Hydroxypropyl guar is preferred.

While theoretically the highest level of hydroxypropyl substitution in guar gum is 3.0 MS such products are not available commercially. For purposes of this invention, however, it is important to have a guar derivative that is compatible with a variety of organic solvents and that is compatible with propylene glycol. Incompatibility of guars not useful for purposes of this invention result in flocculation and reduced clarity. This appears to be true even if the guar is purified such as by the removal of extraneous proteinaceous materials.

It is noted that the selected guars described for this invention are believed to perform better than corresponding celluloses; for example hydroxypropyl guar has advantages over hydroxypropyl cellulose in terms of improved visual aesthetics (no visible particles); and easier dispersal and swelling in a wider range of solvents suitable for dissolving DBS.

The guar functions as a structural integrity enhancer. It contributes to the gelling of the gel, is an antisynerisis aid, adds to structural stability, and improves the aesthetics of the cosmetic product (for example by making it harder). An example of a commercially available guar that works well in this invention is JAGUAR® HP 120 from Rhone-Poulenc, Cranbury, N.J.

The guar is used in an amount of 0.1–1.0%, particularly 0.2–0.5% by weight based on the total weight of the composition.

The third component of the composition is a solvent. The solvent (or solvents) is utilized as a solvent for the DBS and the guar. It is selected so that it is non-reactive (or nearly so) with the DBS and the guar. Whenever an acid catalyst material is present (for example, an antiperspirant active salt is an acid catalyst) the solvent must also be selected so that it is also non-reactive in that system. It is added in sufficient quantity to form the cosmetic composition, for example, in an amount of 99.15–94.0%, particularly 99.05–96.5%, and more particularly 98.8–97.5% by weight based on the total weight of the composition. The solvent forms the base matrix of the solid stick when combined with the gelling agent. The solvent desirably also solubilizes the antiperspirant active, to form a clear product, and can also solubilize other components, in order to produce miscible products which can be formed into transparent gels. Various solvents which can be utilized according to the present invention are disclosed in EP No. 512,770 A1 and PCT No. WO92/19221, each of which has previously been incorporated by reference in their entirety in the present application. Such solvents include (but are not limited to:

(a) dihydroxy aliphatic alcohols containing from 3 to 6 carbon atoms, such as 1,3-propylene glycol, 1,2-propylene glycol, 1,3-butylene glycol, 1,4-butylene glycol and hexylene glycol;

(b) various liquid polyethylene and polypropylene glycols, such a dipropylene glycol, tripropylene glycol, tetrapropylene glycol and methyl propane diol (also called 2-methyl-1,3-propanediol or, more commonly, MPDiol) from Arco Chemical Company, Newtown Square, Pa.;

(c) monohydric alcohols such as ethanol, n-propanol, etc.

(d) mixtures of the individual groups or individual solvents within a single group listed above. The solvents are also described, for example, in U.S. Pat. No. 4,518,582, the contents of which are incorporated herein by reference in their entirety. Particularly preferred solvents include propylene glycol, dipropylene glycol, butylene glycol, hexylene glycol, PPG-10 butanediol, dipropylene glycol, tripropylene glycol, tetrapropylene glycol and MPDiol; and mixtures thereof. More preferred are dipropylene glycol, tripropylene glycol, tetrapropylene glycol and MPDiol.

If it is desired to form cosmetic products with an antiperspirant claim and/or action, an antiperspirant active material should also be included in the composition. Various antiperspirant active materials that can be utilized according to the present invention include conventional aluminum and aluminum/zirconium salts, as well as aluminum/zirconium salts complexed with a neutral amino acid such as glycine, as known in the art. See each of EP No. 512,770A1 and PCT No. WO92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention. Suitable materials include (but are not limited to) aluminum chlorohydroxide, aluminum chloride, aluminum sesquichlorohydroxide, zirconyl hydroxychloride, and aluminum chlorohydrol-propylene glycol complex. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrox gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, for example, in PCT No. WO92/19221, the contents of which are incorporated by reference in their entirety herein.

The amount of antiperspirant active material incorporated in the stick composition of the present invention is, preferably, an antiperspirant effective amount; that is, an amount to reduce the how of perspiration from the location (for example, axillary region of a human) to which the antiperspirant is applied. For deodorant products a level of from 0.5–20%, more particularly 0.5–5.0% by weight based on the entire weight of the composition is used. For an antiperspirant product an amount of 5.0–25%, particularly 5–20%, even more particularly 7–15%, and especially 7–12% by weight based on the total weight of this composition may be used. The amount of antiperspirant material utilized is dependent on the efficacy of the specific antiperspirant material, as well as a maximum amount which avoids a reduction in clarity of the final product.

For embodiments of the invention which contain an antiperspirant (either at a level denominated "deodorant" or at a level denominated "antiperspirant") it is preferred that a stabilizing agent also be included Examples of suitable stabilizing agents include cosmetically acceptable alkali metal salts, bases, amines and other nitrogen containing compounds, particularly guanidine carbonate (described in U.S. Pat. No. 5,490,979 and assigned to the same assignee as this application).

Other agents for reducing malodor may also be included including sodium bicarbonate, and antibacterials. An illustrative antibacterial agent that can be utilized according to the present invention is Triclosan; benzethonium chloride; zinc phenolsulfonate and Triclocarban. Typically, compositions according to the present invention may contain up to about 2% antibacterial agents, preferably about 0.1% to 1.5%, by weight, of the total weight of the composition.

Suitable emollients include cosmetically acceptable ingredients for example, as described in the *CTFA Cosmetic Ingredient Handbook*, edited by J. M. Nikitakis (first edition, 1988) (The Cosmetic, Toiletry and Fragrance Association, Inc., Washington, D.C.) at page 79–81. Emollients may be selected from the group consisting of emollient oils such as a liquid mixture of hydrocarbons which are liquids at ambient temperatures (such as petroleum distillates and light mineral oils), mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate and lauryl lactate; fatty acids such as lauric, myristic, palmitic, stearic, oleic, linoleic, and behenic; fatty alcohols such as lauryl, myristyl, cetyl, isocetyl, stearyl, isostearyl, oleyl, ricinoleyl, erucyl, and 2-octyl dodecanol; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; and hydrocarbons such as petrolatum and squalene.

Particular examples of such emollients include cetyl esters, dioctyl adipate, isopropyl myristate, isopropyl palmitate, mineral oil, PEG esters (for example, PEG-3 lanolate), PPG esters (for example, PPG-26 oleate), propylene glycol esters (for example, propylene glycol isostearate); and PPG-10 butanediol, C12–C15 alkyl lactate, dioctyl sebacate and dimethyl sebacate.

Suitable humectants include cosmetically acceptable ingredients for example, as described in the *CTFA Cosmetic Ingredient Handbook* at pages 81–82. Examples of suitable humectants include glycerin, PEG-6, and sorbitol.

Suitable surfactants include cosmetically acceptable ingredients for example, as described in the *CTFA Cosmetic Ingredient Handbook* at pages 90–97. Examples of such surfactants include: nonionic surfactants such as glyceryl laurate, laureth-3, oleth-10, sorbitan laurate; anionic surfactants such as DEA-oleth-10 phosphate, cocoyl sarcosine, sodium cocoylisethionate; cationic surfactants such as cocamidopropylaimine oxide, dicetyldimonium chloride; and amphoteric surfactants such as cocamidopropyl hydroxysultaine, oleyl betaine, disodium cocoamphodiacetate.

Suitable detackifiers include silicone fluids such as phenyl trimethicone (for example, DOW CORNING® 556 Fluid (Dow Corning Corporation, Midland, Mich.), isopropyl esters, triglycerides, and isostearate esters, dimethyl sebacate, dipropyl sebacate.

Suitable sun screens include octyl methoxycinnamate, aminobenzoic acid, octyl salicylate, oxybenzole and cosmetically acceptable ultraviolet light absorbers for example as listed in the *CTFA Cosmetic Ingredient Handbook* at page 98.

Suitable bug repelling agents include N,N-diethyl-m-toluamide ("DEET") and citronella.

Suitable antisynerisis agents include fumed silica, acrylic polymers and, for deodorants, pectins and gelatins.

Suitable anti-irritants include high molecular weight glycols, for example, di-, tri- and tetrapropylene glycols and mixtures thereof, benzyl alcohol, and aloe vera.

As noted above, the compositions of the present invention can include various known detackifying agents and emollients. Such detackifiers and emollients are disclosed in EP No. 512,770 A1 and PCT No. WO92/19221, the contents of each of which are incorporated herein by reference in their entirety. These agents and emollients prevent stickiness of the compositions after they have dried on the skin surface, and enhance the feel of the compositions and the ease with which they can be applied. Illustrative amounts of the detackifiers and emollients are disclosed in EP No. 512,770 A1 and PCT No. WO92/19221, and include (but are not limited to) 1%–40% by weight, of the total weight of the composition, of one or more emollients and/or detackifiers.

The compositions according to the present invention can also include other, optional, components conventionally incorporated in antiperspirant stick compositions, including (but not limited to) perfumes (fragrances), antibacterial agents, fungistats, pigments, dyes, colorants, ultraviolet absorbers, etc. Illustratively, and not limiting, the perfumes normally employed in cosmetic compositions can be employed in compositions of the present invention, if desired, with concentrations of such perfumes typically being up to about 2%, for example, about 0.5% to 2%, by weight, of the total weight of the composition. Compositions according to the present invention are preferably anhydrous, although they can contain small amounts (for example, up to 0.5% by weight, of the total weight of the composition) of water.

The amounts of each of the optional ingredients are selected on the basis of the solvent vehicle used and the presence or absence of an antiperspirant active. For example, in a typical formulation the following ingredients may be combined:

a) from 40–96.65% solvent such as propylene glycol;

b) from 0.75–5.0% DBS;

c) from 0.1–1.0% , of a guar as described above;

d) from 1–40% (particularly 1–25%) of one or more antitack agents/emollients with some solvency in the solvent and selected from the group consisting of C12–C15 alkyl benzoate (for example, FINSOLV TN from Finetex, Elmwood Park, N.J.), esters of sebacic acid, functional silicones (for example, GE SF 1388 from General Electric, Waterford, N.Y.), PPG-10 butanediol (PROBUTYL DB-10 from Croda Inc., Edison, N.J.).

e) from 1–7% (particularly 2–3%) clarifying agent (for example, see U.S. Pat. No. 5,458,880 to Kasat et al for a description of suitable clarifying agents such as SANDOPAN LA-24 LIQUID from Clariant Corporation, Charlotte, N.C.);

f) from 0–10% of a processing aid selected from the group consisting of PEG-6, propyl carbonate, dipropyl carbonate, tripropyl carbonate and tetrapropyl carbonate;

g) from 0.5–25% of an antiperspirant active;

h) from 0–2% of other optional ingredients such as fragrances, dyes, etc.

Various types of antiperspirant and/or deodorant products can be made by using the invention described above in the form of sticks.

A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear, for example, stick or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectro-photometer. As to this definition of clear, see European Patent Application Publication No. 291,334 A2. Thus, according to the present invention, there are differences between transparent (clear), translucent and opaque compositions.

The term "clear" is used herein in its usual dictionary definition. That is, a clear antiperspirant stick, like glass, allows for ready viewing of objects behind it. By contrast, a translucent antiperspirant stick, although allowing light to pass throughout it, causes the light to scatter, making it impossible to clearly identify objects behind it. Compositions of the present invention may be formed, for example, so that the transmittance of light as evaluated by a turbidimeter have values in the range of 30–950 nephelometric turbidity units (NTU), preferably below 800 NTU, more preferably below 200 NTU and particularly below 100 NTU. Equipment such as Model 965-10A Digital Direct-Reading Turbidimeter from Orbeco Analytical Systems, Inc., Farmingdale, N.Y., using acceptable accepted test protocols such as ASTM D 5180-93 entitled "Standard Test Method for Quantitative Test for Turbidity in Clear Liquids; ASTM D 1889-94 entitled "Standard Test Method for Turbidity of Water"; and selected methods from *Standard Methods for the Examination of Water and Wastewater* (American Public Health Association Washington D.C., 1995): No. 2130 "Turbidity" can be used.

The invention also includes a method of making such cosmetic compositions. In particular, it is important that the guar be predispersed in the solvent and solvent with heat before combining it with the DBS. The temperature will depend on the solvent used. The predispersed guar is then combined with DBS and the other ingredients to be added to the cosmetic composition. It is important to use equipment that will provide a suitable vortex so that the composition is formed with minimal lumps while not experiencing shear that is so high as to interfere with the formation of a geld product.

One particular method is as follows:

Gel Phase (a) charge the formula amount of the solvent (for example, propylene glycol) to a main mixing vessel and begin agitation at a speed to create a sufficient vortex;

(b) slowly sprinkle in the guar (for example, hydroxypropyl guar);

(c) once the guar is homogeneously dispersed, begin heating the mixture to 60 degrees C. to facilitate complete solvation with continued agitation;

(d) slowly add the amount of DBS to be included in the formulation at 60 degrees C.;

(e) continue heating and mixing until the temperature is in the range of 95–105 degrees C. and mix until all of the DBS is dissolved into solution.

Actives Phase (a) add the actives and guanidine carbonate to a suitable mixing vessel containing the solvent for the active. Heat to a temperature in the range of 95–105 degrees C. with agitation;

(b) charge to the Gel Phase described previously.

Fragrance/Colors (a) once the mixture in the main mixing vessel is homogeneous, begin cooling to 10 degrees C. above the titer (gellation temperature);

(b) charge the fragrance/colors with continued agitation;

(c) once fragrance and colors are incorporated into the mixture, container can be filled with the mixture at 5 degrees above the titer point and the products may then be cooled in the containers.

The use of two separate phases can also be used in a semi-continuous process in which the two phases are kept separate until they are combined prior to adding fragrance by metering into a hot product steam which intimately mixes each component by in-line static mixer.

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear, for example, stick or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88Spectro-photometer. As to this definition of clear, see European Patent Application Publication No. 291.334 A2. Thus, according to the present invention, there are differences between transparent (clear), translucent and opaque compositions.

In a particular embodiment of the invention a polyamide is used to form a solid composition of the present invention which is a clear, or at least a translucent, gel or stick (for example, antiperspirant gel or stick composition).

Throughout the present specification, where compositions are described as including or comprising specific components, it is contemplated by the inventors that compositions of the present invention also consist essentially of, or consist of, the recited components. Accordingly, throughout the disclosure any described composition can consist essentially of, or consist of, the recited components.

The antiperspirant solid gel stick composition according to the present invention is used as such stick compositions are conventionally used. Specifically, the composition can be filled into a dispensing container as done conventionally, with the composition hardening in such container. The composition is used by elevating and exposing the stick out of the dispensing container, as done conventionally, and applying the product to, for example, axillary regions of the body, so as to provide antiperspirant protection.

In the following are disclosed various compositions according to the present invention. These compositions contain guanidine compounds as stabilizers. In the following examples, which are illustrative and not limiting, as well as throughout the rest of this disclosure, the names of the components are names as in the *CTFA International Cosmetic Ingredient Dictionary* (4th Ed. 1991), and amounts are percent by weight, of the total weight of the composition.

EXAMPLES

The following Examples are offered as being illustrative of the invention but should not be construed as limitations thereon. In the Examples and elsewhere in this application, chemical terms have their usual and customary meanings and all percents are in weight percents based on the weight of the total composition unless indicted otherwise. For the following Examples the following materials were used:

Example 1

Gel Phase

Propylene glycol (51.3 g) is charged to the gel phase tank equipped with suitable heating and agitation capabilities. A polyethylene glycol (PEG-6) (2.00 g of CARBOWAX SENTRY POLYETHYLENE GLYCOL 300 from Union Carbide Chemical, Danbury, Conn.); PPG-10 butanediol (1.00 g of PROBUTYL DB-10 from Croda Inc., Parsippany, N.J.); C12–C15 alkyl lactate (0.90 g of CERAPHYLL 41 from ISP Van Dyk, Wayne, N.J.); Dimethicone copolyol (0.90 g of GE SF-1388 from General Electric Company, Waterford, N.Y.); dioctyl sebacate (0.75 g of UNIMATE DOS from Wayne, N.J.); dimethyl sebacate (0.75 g of UNIMATE DMS from Union Camp); are combined in the listed order into the gel phase tank. Each ingredient is thoroughly mixed in with the contents of the tank and the mixture is formed into a homogeneous mixture before the next ingredient is added. Hydroxypropyl guar (0.40g) is sprinkled into the tank and mixing with sufficient agitation to prevent settling is continued until the guar is well dispersed. Heating is initiated until the mixture reaches a temperature of 85 degrees C. Once the batch attains a temperature of 85 degrees C. DBS (0.50 g of a carboxylated surfactant such as sodium laureth-13 carboxylate (SANDOPAN LA-24 LIQUID from Clariant Corporation, Charlotte, N.C.) is sprinkled in. Heating is continued for the gel phase until a temperature of 95 degrees C.±5 degrees C. is attained. That temperature is maintained and mixing is continued until all of the DBS is dissolved.

Actives Phase

A self-buffered active aluminum zirconium salt with zinc glycinate in mixed glycols (39.4 g of 28% active aluminum zirconium in propylene glycol/dipropylene glycol guanidine carbonate) is charged to an actives tank which is a separate mixing and heating vessel of appropriate size. Mixing is initiated and heating is started until the temperature reaches 60 degrees C.±5 degrees C.

Combined Phases

Just prior to the filling operation the Gel Phase, Actives Phase, and color/fragrance (1.00 g of fragrance) are each metered into a jacketed surge tank. Filling takes place at 5 degrees C. above the titer.

Examples 2–4

Texture Profile Analysis

Texture Profile Analysis (TPA) was conducted using the TA-XT2 equipment from Texture Technologies Corporation, Scarsdale, N.Y. The instrument uses two passes of a probe to penetrate a preset distance into a test stick at a controlled velocity for a set time period. As explained in their manual entitled *Stable Micro Systems, Texture Expert* (version 1.0), Issue 2, Chapter 15 "Sample Files" pages 119–122 and FIGS. 44 and 45 (19__(date)), the test results in a Texture Profile Analysis which is a plot of Force (grams) versus Time (seconds) at a selected depth of penetration (here 2.5 mm was used). The TPA is then reviewed for various attributes such as springiness, hardness, cohesiveness, adhesiveness, resilience, etc. The TPA uses Force versus Time to create a graph and numerical values for the various attributes. The numerical values for the attributes are calculated from the data and areas under the curves in the graph. With this method one can compare differences between various types of stick antiperspirants and deodorants. When running the TPA test it is important to control distance of compression, duration of compression and velocity of the probe. Note that some of the terms have units associated with them and others such as springiness, cohesiveness and resilience are dimensionless.

For the samples shown in Table 1, Example 2 was the control sample made as described below without hydroxypropyl cellulose or hydroxypropyl guar. Example 3 was the sample with hydroxypropyl guar (JAGUAR® HP-120 from Rhone-Poulenc, Cranbury, N.J.). Example 4 was the sample with hydroxypropyl cellulose (KLUCEL® MFF from Hercules Inc., Aqualon Division, Wilmington, Del.). Table 1 lists the data obtained for the properties described using laboratory observations and shows the superiority of the stick made with the guar. The data in Table 1 is an average of three different measurements.

Example 2
Control

A control sample was made using the method of Example 1 but substituting extra propylene glycol for the guar. The results of the Texture Profile Analysis is shown in Table 1.

Example 3
Guar

The method of Example 1 was repeated with three different addition levels of guar (JAGUAR® HP 120, at levels of 0.2%, 0.4% and 0.8% by weight based on the total weight of the composition). Extra propylene glycol was included as needed to make 100%. The results of the Texture Profile Analyses are shown in Table 1.

Example 4
Cellulose

The method of Example 1 was repeated with three different addition levels of cellulose (KLUCEL® MFF at levels of 0.2%, 0.4% and 0.8% by weight based on the total weight of the composition). Extra propylene glycol was included as needed to make 100%. The results of the Texture Profile Analyses are shown in Table 1.

(b) a derivatized guar having a level of hydroxyalkylation of 0.4–1.5 molar substitution; and (c) a solvent selected so that is does not react with the dibenzylidene sorbitol itself or in the presence of dibenzylidene sorbitol and an acid catalyst.

2. An anhydrous gel composition as claimed in claim 1 wherein the composition further comprises at least one member of the group consisting of:

a) an antiperspirant active;
b) an agent for reducing malodor;
c) a stabilizing agent;
d) an antibacterial agent;
e) an emollient;
f) a detackifier;
g) a sun screen;
h) a bug repelling agent;
i) an antisynerisis agent;
j) an anti-irritant;
k) fragrance; and
l) coloring.

3. An anhydrous gel composition as claimed in claim 1 made by combining:

(a) 0.75–5.0 percent dibenzylidene sorbitol;
(b) 0.1–1.0 percent of an hydroxy $C_3$–$C_4$ linear or branched alkyl guar having a level of hydroxylation of 0.4–1.5 molar substitution; and
(c) 94.0–99.15 of the solvent based on the total weight of the composition.

4. An anhydrous gel composition as claimed in claim 3 wherein the solvent is selected from the group consisting of (a) dihydroxy aliphatic alcohols containing from 3 to 6 carbon atoms,
(b) liquid polyethylene and polypropylene glycols;
(c) monohydric alcohols;
(d) mixtures of any of the members of groups (a), (b) and (c).

5. An anhydrous gel composition as claimed in claim 4 wherein the dihydroxy aliphatic alcohols are members of the group consisting of 1,3-propylene glycol, 1,2-propylene glycol, 1,3-butylene glycol, 1,4-butylene glycol and hexylene glycol.

TABLE 1

| Sample | Springiness | Cohesiveness | Gumminess (grams) | Adhesiveness (gram-mm) | Hardness (grams) | Resilience |
| --- | --- | --- | --- | --- | --- | --- |
| Ex. 2 | 0.668 | 0.172 | 172 | −29 | 1025 | 0.074 |
|  | +/− 0.057 | +/− 0.052 | +/− 40.3 | +/− 6.913 | +/− 164 | +/− 0.027 |
| Ex. 3 | 0.828 | 0.209 | 424 | −63 | 2018 | 0.128 |
| 0.2% | +/− 0.061 | +/− 0.019 | +/− 64.5 | +/− 13.8 | +/− 170 | +/− 0.022 |
| Ex. 4 | 0.874 | 0.196 | 234 | −90 | 1198 | 0.064 |
| 0.2% | +/− 0.099 | +/− 0.011 | +/− 12.5 | +/− 23.1 | +/− 113 | +/− 0.002 |
| Ex. 3 | 0.933 | 0.189 | 351 | −62 | 1848 | 0.111 |
| 0.4% | +/− 0.026 | +/− 0.014 | +/− 48.8 | +/− 12.9 | +/− 137 | +/− 0.016 |
| Ex. 4 | 0.865 | 0.169 | 231 | −51 | 1371 | 0.071 |
| 0.4% | +/− 0.005 | +/− 0.013 | +/− 29.3 | +/− 9.0 | +/− 114 | +/− 0.015 |
| Ex. 3 | 0.733 | 0.293 | 1020 | −24 | 3520 | 0.266 |
| 0.8% | +/− 0.212 | +/− 0.073 | +/− 191.9 | +/− 14.0 | +/− 310 | +/− 0.102 |
| Ex. 4 | 0.888 | 0.246 | 906 | −19 | 3687 | 0.220 |
| 0.8% | +/− 0.007 | +/− 0.011 | +/− 56.4 | +/− 5.3 | +/− 175 | +/− 0.011 |

What is claimed is:

1. An anhydrous gel composition made by combining ingredients comprising:

(a) dibenzylidene sorbitol;

6. An anhydrous gel composition as claimed in claim 4 wherein the monohydric alcohols have two or three carbon atoms.

7. An anhydrous gel composition as claimed in claim 4 wherein the polyethylene and polypropylene glycols are members of the group consisting of dipropylene glycol, tripropylene glycol, tetrapropylene glycol and methyl propane diol.

8. An anhydrous gel composition as claimed in claim 2 comprising an antiperspirant active selected from the group consisting of aluminum chlorohydroxide, aluminum chloride, aluminum sesquichlorohydroxide, zirconyl hydroxychloride, and aluminum chlorohydrol-propylene glycol complex.

9. An anhydrous gel composition as claimed in claim 2 comprising an antiperspirant active selected from the group consisting of aluminum chlorohydrate; aluminum chloride; aluminum sesquichlorohydrate; zirconyl hydroxychloride; aluminum-zirconium glycine complex selected from the group consisting of aluminum zirconium trichlorohydrex gly, aluminum zirconium pentachlorohydrex gly, aluminum zirconium tetrachlorohydrex gly and aluminum zirconium octochlorohydrex gly; aluminum chlorohydrox PG, aluminum chlorohydrex PEG, aluminum dichlorohydrex PG, and aluminum dichlorohydrex PEG.

10. An anhydrous gel composition as claimed in claim 4 wherein the solvent is selected from the group consisting of propylene glycol, dipropylene glycol, butylene glycol, hexylene glycol, PPG-10 butanediol, dipropylene glycol, tripropylene glycol, tetrapropylene glycol and MPDiol; and mixtures thereof.

11. An anhydrous gel composition as claimed in claim 10 wherein the solvent is selected from the group consisting of dipropylene glycol, tripropylene glycol, tetrapropylene glycol and MPDiol.

12. A cosmetic composition for reducing body malodor comprising a composition an anhydrous gel composition as claimed in any one of claims 1-11.

13. An anhydrous gel composition as claimed in claim 8 or claim 9 wherein the antiperspirant active is added in an amount of 0.5-20 by weight based on the total weight of the composition.

14. An anhydrous gel composition as claimed in claim 8 or claim 9 wherein the antiperspirant active is added in an amount of 0.5-5.0% by weight based on the entire weight of the composition.

15. An anhydrous gel composition as claimed in claim 8 or claim 9 wherein the antiperspirant active is added in an amount of 5.0-25% based on the total weight of the composition.

16. An anhydrous gel composition as claimed in claim 8 or claim 9 wherein the antiperspirant active is added in an amount of 5-20% by weight based on the total weight of this composition may be used.

17. An anhydrous gel composition as claimed in claim 8 or claim 9 wherein the stabilizing agent is selected from the group consisting of cosmetically acceptable alkali metal salts, bases, aminies and guanidine carbonate.

18. An anhydrous gel composition as claimed in claim 2 made by adding at least one member from the group consisting of sodium bicarbonate, Triclosan, benzethonium chloride, zinc pheniolsulfoniate and Triclocarban.

19. An anhydrous gel composition as claimed in claim 2 wherein the composition is made by combining ingredients comprising 40–96.65% solvent; 0.75–5.0% dibenzilidene sorbitol; and 0.1–1.0% guar.

20. An anhydrous gel composition as claimed in claim 2 made by combining:

a) from 40–96.65% solvent;

b) from 0.75–5.0% dibenzilidene sorbitol;

c) 0.1–1.0% guar;

d) from 1–40% of at least one anititack agent or emollient soluble in the solvent;

e) from 1–7% clarifying agent;

f) from 0–10% of a processing aid;

g) from 0.5–25% of an antiperspirant active; and h) from 0–2% of an optional ingredient selected from the group consisting of fragrances and dyes.

21. An anhydrous gel composition as claimed in any one of claims 1, 2, 3, 19 or 20 wherein the guar is hydroxypropyl guar.

22. An anhydrous gel composition as claimed in any one of claims 1, 2, 3, 19 or 20 wherein the solvent is selected from the group consisting of:

(a) dihydroxy aliphatic alcohols containing from 3 to 6 carbon atoms;

(b) polyethylene and polypropylene glycols;

(c) monohydric alcohols;

(d) mixtures of individual groups or individual solvents from groups (a), (b) and (c).

23. An anhydrous gel composition as claimed in any one of claims 1, 2, 3, 19 or 20 wherein the solvent is selected from the group consisting of: (a) 1,3-propylene glycol, 1,2-propylene glycol, 1,3-butylene glycol, 1,4-butylene glycol and hexylene glycol;

(b) dipropylene glycol, tripropylene glycol, tetrapropylene glycol and methyl propane;

(c) ethanol and n-propanol and (d) mixtures of the individual groups or individual solvents from groups (a), (b) and (c) within a single group listed above.

24. An anhydrous gel composition as claimed in any one of claims 1, 2, 3, 19 or 20 wherein the solvent is selected from the group consisting of: propylene glycol, dipropylene glycol, butylene glycol, hexylene glycol, PPG-10 butanediol, dipropylene glycol, tripropylene glycol, tetrapropylene glycol, MPDiol; and mixtures thereof.

25. An anhydrous gel composition comprising:

(a) dibenzylidene sorbitol;

(b) a derivatized guar having a level of hydroxyalkylation of 0.4–1.5 molar substitution; and (c) a solvent selected so that is does not react with the dibenzylidene sorbitol itself or in the presence of dibenzylidene sorbitol and an acid catalyst.

26. An anhydrous gel composition as claimed in claim 25 further comprising at least one member of the group consisting of:

a) an antiperspirant active;

b) an agent for reducing malodor;

c) a stabilizing agent;

d) an antibacterial agent;

e) an emollient;

e) a detackifier;

g) a sun screen;

h) a bug repelling, agent;

i) an antisynerisis agent;

j) an anti-irritant;

k) fragrance; and l) coloring.

27. An anhydrous gel composition as claimed in claim 26 comprising:

a) from 40–96.65% solvent;

b) from 0.75–5.0% dibenzilidene sorbitol;

c) from 0.1–1.0% guar;

d) from 1–40% of at least one antitack agent or emollient soluble in the solvent;

e) from 1–7% clarifying agent;

f) from 0–10% of a processing aid;

g) from 0.5–25% of an antiperspirant active; and h) from 0–2% of an optional ingredient selected from the group consisting of fragrances and dyes.

28. A cosmetic composition for reducing body malodor comprising an anhydrous gel composition as claimed in any one of claims 1–11 wherein the cosmetic composition is clear.

29. A cosmetic composition for reducing body malodor comprising a composition an anhydrous gel composition as claimed in any one of claims 18, 19, 25, 26, or 27 wherein the cosmetic composition is clear.

* * * * *